(12) United States Patent
Collins et al.

(10) Patent No.: US 11,534,290 B2
(45) Date of Patent: Dec. 27, 2022

(54) MODULAR IOL DESIGN

(71) Applicant: Alcon Inc., Fribourg (CH)

(72) Inventors: Stephen John Collins, Fort Worth, TX (US); Philip Matthew McCulloch, Mansfield, TX (US); Rudolph F. Zacher, Trabuco Canyon, TX (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 17/210,946

(22) Filed: Mar. 24, 2021

(65) Prior Publication Data
US 2021/0298892 A1   Sep. 30, 2021

Related U.S. Application Data

(60) Provisional application No. 63/000,553, filed on Mar. 27, 2020.

(51) Int. Cl.
*A61F 2/16* (2006.01)
(52) U.S. Cl.
CPC ...... *A61F 2/1613* (2013.01); *A61F 2002/169* (2015.04); *A61F 2002/1696* (2015.04); *A61F 2002/16901* (2015.04); *A61F 2250/006* (2013.01)

(58) Field of Classification Search
CPC .............. A61F 2/1613; A61F 2/1648; A61F 2002/169; A61F 2002/16901; A61F 2002/16902
See application file for complete search history.

(56) References Cited

U.S. PATENT DOCUMENTS

| 8,728,158 B2 * | 5/2014 | Whitsett ............... A61F 2/1613 |
| | | 623/6.43 |
| 9,421,088 B1 | 8/2016 | Kahook |
| 2003/0204254 A1 | 10/2003 | Peng et al. |
| 2009/0125106 A1 | 5/2009 | Weinschenk, III et al. |
| 2013/0190868 A1 * | 7/2013 | Kahook ............... A61F 2/1613 |
| | | 623/6.38 |
| 2017/0000602 A1 | 1/2017 | Sohn et al. |
| 2017/0319332 A1 | 11/2017 | Kahook |

* cited by examiner

*Primary Examiner* — William H Matthews

(57) ABSTRACT

A modular intraocular lens (IOL) with a ring configured to prevent glare artifacts. The ring includes a flange on the posterior rim, in which an anterior surface on the flange has a first profile and a posterior surface of the flange has a second profile non-parallel with the first profile. Non-parallel surfaces of the flange can be configured to defocus light transmitted at off-axis angles through an optic and the flange.

12 Claims, 4 Drawing Sheets

MODULAR IOL DESIGN

PRIORITY CLAIM

This application claims the benefit of priority of U.S. Provisional Patent Application Ser. No. 63/000,553 titled "MODULAR IOL DESIGN," filed on Mar. 27, 2020, whose inventors are Stephen John Collins, Philip Matthew McCulloch, and Rudolph F. Zacher, which is hereby incorporated by reference in its entirety as though fully and completely set forth herein.

FIELD

The present disclosure relates generally to the field of modular intraocular lenses (IOLs), and more particularly to an IOL comprising an optic supported by a ring with features to reduce or even prevent glare artifacts.

BACKGROUND

The eye has been described as an organ that reacts to light for several purposes. As a conscious sense organ, the eye allows vision. Rod and cone cells in the retina allow conscious light perception and vision including color differentiation and the perception of depth. In addition, the human eye's non-image-forming photosensitive ganglion cells in the retina receive light signals which affect adjustment of the size of the pupil, regulation and suppression of the hormone melatonin, and entrainment of the body clock.

The crystalline lens is a transparent, biconvex structure in the eye that, along with the cornea, helps to refract light to be focused on the retina. The lens, by changing its shape, functions to change the focal distance of the eye so that it can focus on objects at various distances, thus allowing a sharp real image of the object of interest to be formed on the retina. This adjustment of the lens is known as accommodation and is similar to the focusing of a photographic camera via movement of its lenses.

When age or disease causes the lens to become less transparent (e.g., cloudy), vision deteriorates because of the diminished light, which can be transmitted to the retina. This deficiency in the lens of the eye is medically known as a cataract. An accepted treatment for this condition is surgical removal of the lens from the capsular bag and placement of an artificial intraocular lens (IOL) in the capsular bag. In the United States, the majority of cataractous lenses are removed by a surgical technique called phacoemulsification. During this procedure, an opening (capsulorhexis) is made in the anterior side of the capsular bag and a thin phacoemulsification-cutting tip is inserted into the diseased lens and vibrated ultrasonically. The vibrating cutting tip liquefies or emulsifies the lens so that the lens may be aspirated out of the capsular bag. The diseased lens, once removed, is replaced by an IOL.

Some conventional IOLs are single focal length IOLs. Single focal length IOLs have a single focal length or single power. Objects at the focal length from the eye/IOL are in focus, while objects nearer or further away may be out of focus. Although objects are in perfect focus only at the focal length, objects within the depth of field (within a particular distance of the focal length) are still acceptably in focus for the patient to consider the objects in focus.

SUMMARY

Embodiments of a modular intraocular lens (IOL) disclosed herein are unique in that a ring supporting an optic has a flange to defocus light that may otherwise cause glare. A modular IOL comprises an optic and a base for supporting the optic. The optic has an anterior surface, a posterior surface and a thickness configured to focus light at a focal length. The base comprises a ring formed with an anterior rim sized with an inner diameter to allow a surgeon to insert the optic, a recess for seating the optic in the base, and a posterior rim with a flange defining an inner diameter suitable to prevent the optic from passing through the ring. The flange has a unique geometry to defocus light that enters the IOL off-axis and is transmitted through the optic and the flange.

Embodiments overcome the challenges of creating a modular optical unit that can be assembled and disassembled in the capsular bag by a surgeon, and that also minimizes the possibility of glare caused by off-axis light passing through the optic and the posterior rim of a ring.

A modular IOL comprising an optic and base minimizes the cross-sectional area to allow for a smaller incision than incisions necessary for full IOLs. A base formed with a ring comprising an anterior rim, a posterior rim, and inwardly facing recess allows the surgeon to seat the optic in the base. A ring with a flange with an anterior surface with a first profile and a posterior surface with a second profile that is non-parallel with the first profile may avoid or mitigate plate effects that could cause glare.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

DETAILED DESCRIPTION

Reference will now be made in detail to examples of the present disclosure, which are illustrated in the accompanying drawings. Wherever possible, the same reference numbers will be used throughout the drawings to refer to the same or like parts. In the discussion that follows, relative terms such as "about," "substantially," "approximately," etc.

are used to indicate a possible variation of .+−.10% in a stated value, numeric or otherwise, unless other variations are indicated.

The exemplary embodiments relate to ophthalmic devices such as IOLs and contact lenses. The following description is presented to enable one of ordinary skill in the art to make and use the invention and is provided in the context of a patent application and its requirements. Various modifications to the exemplary embodiments and the generic principles and features described herein will be readily apparent. The exemplary embodiments are mainly described in terms of particular methods and systems provided in particular implementations. However, the methods and systems will operate effectively in other implementations. Phrases such as "exemplary embodiment", "one embodiment" and "another embodiment" may refer to the same or different embodiments as well as to multiple embodiments. The embodiments will be described with respect to systems and/or devices having certain components. However, the systems and/or devices may include more or less components than those shown, and variations in the arrangement and type of the components may be made without departing from the scope of the invention. The exemplary embodiments will also be described in the context of particular methods having certain steps. However, the method and system operate effectively for other methods having different and/or additional steps and steps in different orders that are not inconsistent with the exemplary embodiments. Thus, the present invention is not intended to be limited to the embodiments shown but is to be accorded the widest scope consistent with the principles and features described herein.

Modular IOLs—Overview

Figure 1:
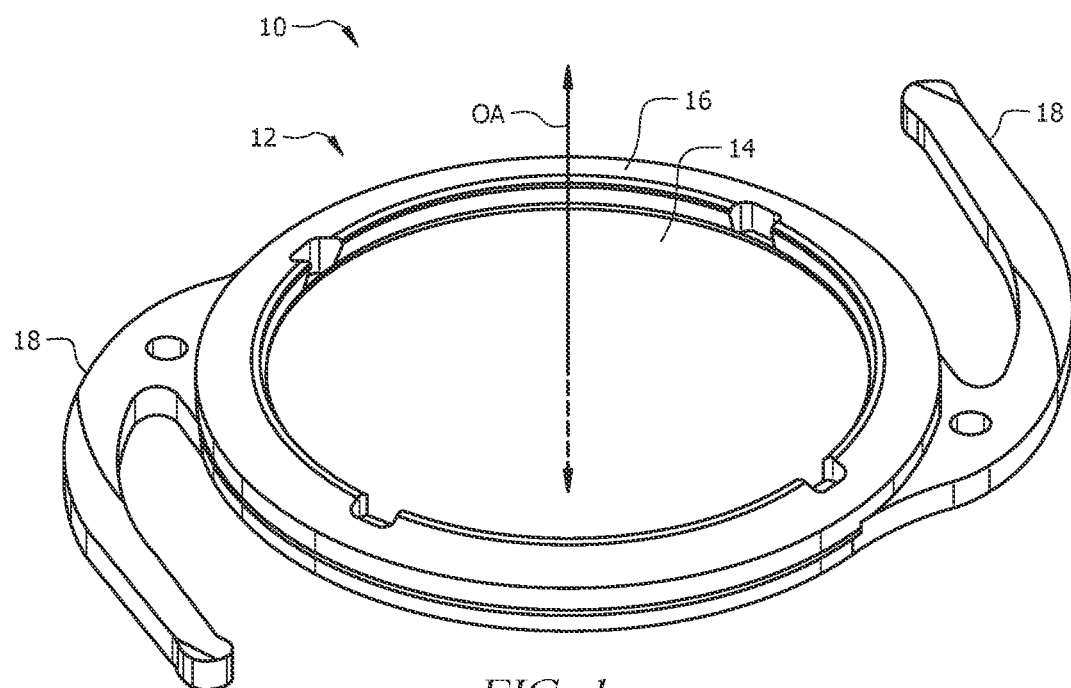
FIG. 1 depicts a perspective view of a modular IOL.

FIG. 1 depicts a perspective view of a modular intraocular lens (IOL) 10 in which embodiments disclosed herein may be implemented. IOL 10 generally comprises base 12 and optic 14. Base 12 is formed with annular ring 16 and haptics 18. Optic 14 is seated in ring 16. Haptics 18 may position and hold ring 16 in the capsular bag to ensure an optical axis (OA) of optic 14 is aligned properly for the patient.

Figure 2:
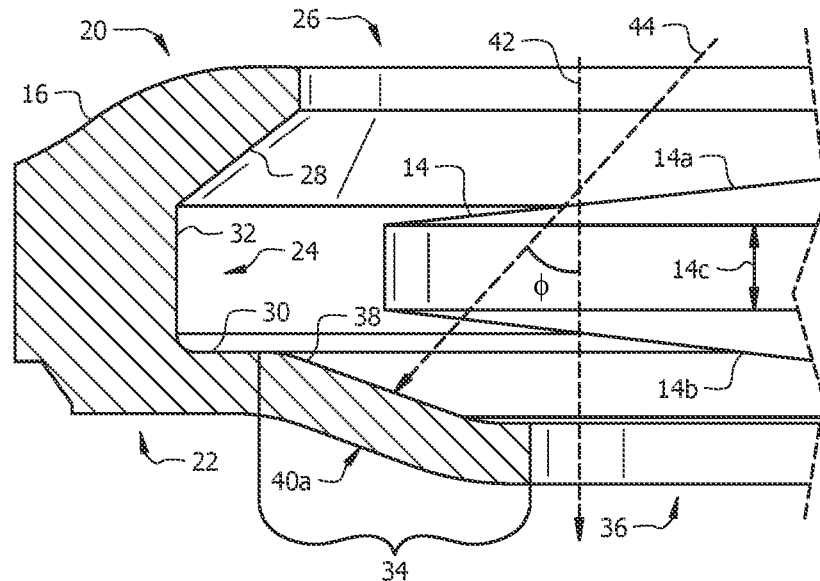
FIG. 2 depicts a partial close-up side view of a modular IOL with an optic seated in a ring, and further depicts a flange in which the flange anterior and posterior surfaces are parallel.
Figure 3:
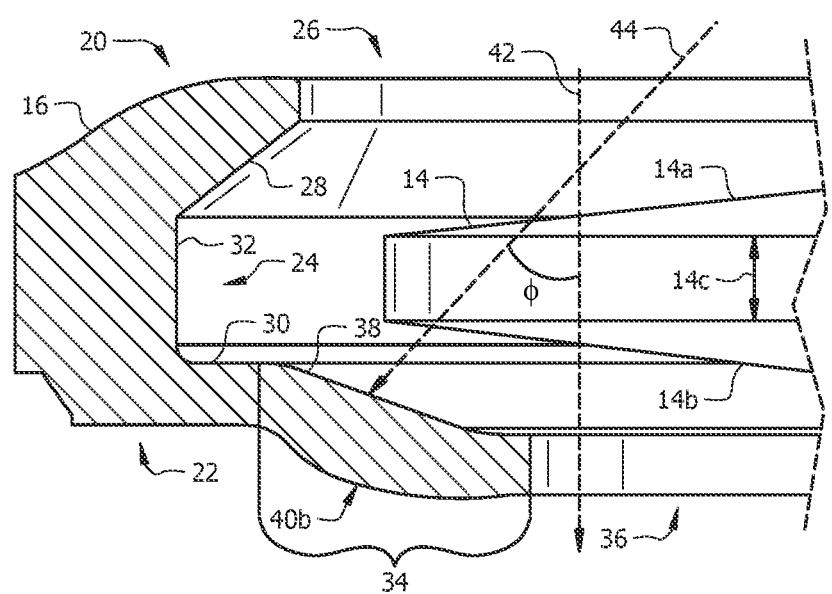
FIG. 3 depicts a partial close-up side view of a modular IOL with an optic seated in a ring, and further depicts a flange in which the flange anterior and posterior surfaces are non-parallel.

FIGS. 2 and 3 depict partial close-up cross-sectional views of modular IOL 10 with optic 14 seated in ring 16.

Optic 14 comprises anterior surface 14a and posterior surface 14b separated by an optic thickness 14c. The radius of curvature of anterior surface 14a, the radius of curvature of posterior surface 14b and optic thickness 14c are selected to focus light passing through IOL 10 at a focal length, described below in greater detail.

As depicted in FIGS. 2 and 3, ring 16 comprises anterior rim 20 and posterior rim 22, wherein anterior rim 20 and posterior rim 22 form inwardly facing recess 24 for seating optic 14. Anterior rim 20 is formed with anterior rim opening 26 sized to allow a surgeon to insert optic 14 into ring 16. A diameter of anterior rim opening 26 may be less than a diameter of optic 14 to prevent optic 14 from exiting ring 16 via anterior rim opening 26 post-implantation.

Inwardly-facing recess 24 may be defined by anterior rim inner surface 28, posterior rim anterior surface 30, and outer surface 32. When optic 14 is fully seated in recess 24, anterior rim inner surface 28, posterior rim anterior surface 30 and outer surface 32 form a geometry that may limit movement of optic 14 relative to ring 16 in anterior, posterior and radial directions.

Posterior rim 22 includes posterior rim anterior surface 30 and further includes flange 34, wherein an inner diameter of flange 34 defines posterior rim opening 36. Flange 34 is formed such that the diameter of posterior rim opening 36 is less than the diameter of optic 14 to prevent optic 14 from passing through ring 16 during implantation and to prevent optic 14 from exiting ring 16 post-implantation.

FIGS. 2 and 3 further depict variations in ring 16, wherein FIG. 3 depicts ring 16 with one embodiment of flange 34 formed to reduce or even prevent glare, as compared to the flange 34 of ring 16 of FIG. 2. As depicted in FIGS. 2 and 3, flange 34 comprises flange anterior surface 38 and flange posterior surface 40 defined between the inner diameter of flange 34 and an outer diameter of flange 34 (which generally refers to a diameter where flange anterior surface 38 transitions to posterior rim anterior surface 30). In both of FIGS. 2 and 3, flange anterior surface 38 and flange posterior surface 40a and 40b are formed with at least portions having curved profiles, with flange anterior surface 38 formed as a concave surface and flange posterior surface 40a and 40b formed at least partially as a convex surface. However, FIG. 2 depicts IOL 10 with flange posterior surface 40a having a profile parallel with flange anterior surface 38 and FIG. 3 depicts IOL 10 with flange posterior surface 40b having a profile non-parallel with flange anterior surface 38. The profiles of flange anterior surface 38 and flange posterior surface 40b may be shaped to reduce or possibly prevent glare, as discussed below.

Glare Due to Off-Axis Light Transmitted Through the Optic and the Flange

As mentioned above, optic 14 is formed with optic anterior surface 14a and optic posterior surface 14b and has an optical axis (OA). Light 42 that is aligned with the optical axis or at an angle less than a threshold incident angle ($\phi$) relative to the optical axis enters IOL 10 via anterior rim opening 26, is transmitted through optic 14, and exits IOL 10 via posterior rim opening 36 focused at a desired focal length. Ideally, in an eye with IOL 10, both the light 42 aligned with the optical axis and the off-axis light 44 are focused at a desired focal length. However, off-axis light 44 that enters IOL 10 at an incident angle equal to or greater than the threshold incident angle ($\phi$) relative to the optic axis is transmitted through optic 14 and is also transmitted through flange 34 or some other mechanical feature. Transmission of off-axis light 44 through flange 34 may delay the focus of off-axis light 44 onto the retina, which may be perceived as glare. The threshold incident angle ($\phi$) at which off-axis light 44 is transmitted through optic 14 and flange 34 may depend on one or more of the materials or dimensions of optic 14 and flange 34. For example, in some modular IOLs 10, the threshold incident angle ($\phi$) may be greater than 25 degrees, whereas in other modular IOLs 10, the threshold incident angle ($\phi$) may be greater than 30 degrees.

Flange Anterior and Posterior Surface Profiles Formed to Reduce or Even Prevent Glare To reduce or even prevent glare or other unwanted effects of off-axis light 44 passing through optic 14 and flange 34, flange 34 depicted in FIG. 3 comprises flange anterior surface 38 having a first profile and flange posterior surface 40b having a second profile that is non-parallel with the first profile. For example, the flange posterior surface 40b may have a profile or shape including a protruding or extending convex curvature.

Figure 4A:
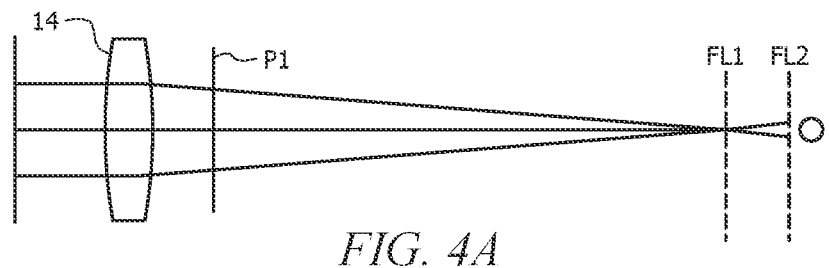
FIG. 4A depicts a simplified diagram of light transmitted through an optic and a thin plate to a focus (FL1), illustrating how light is expected to be transmitted through an IOL in an eye.
Figure 4B:
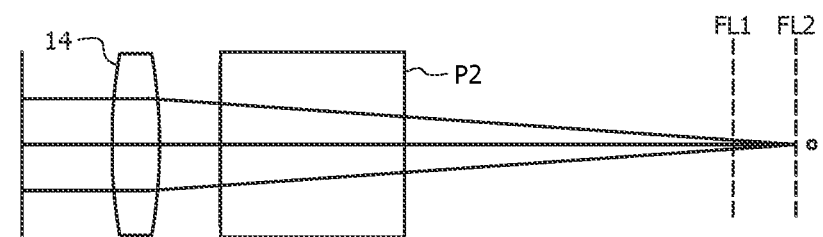
FIG. 4B depicts a simplified diagram of light transmitted through the optic and a thick plate that focuses the light at a second focus (FL2) farther from the optic, illustrating how mechanical features in an IOL may result in plate effect that could result in off-axis light being perceived as glare.

To aid in understanding the benefits of IOL 10 formed with flange 34 having a profile for flange posterior surface 40b non-parallel with a profile for flange anterior surface 38, a discussion of plate effect is described with respect to FIGS. 4A and 4B. FIG. 4A depicts a first simplified diagram of light passing through optic 14 and a thin plate (i.e., the thickness is approximately zero), illustrating how light 42 is expected to be transmitted through IOL in an eye. As depicted in FIG. 4A, collineated light leaves a light source and passes through optic 14. Optic 14 focuses the light at a first rate of convergence towards a point at a first focal length ($FL_1$) until the light encounters plate $P_1$. If the thickness of plate $P_1$ is substantially zero, the light continues at substantially the first rate of convergence until it reaches a point at the first focal length (FL1). In the human eye, the first focal length corresponds to the retina.

FIG. 4B depicts a simplified diagram of light transmitted through optic 14 and a thick plate that focuses the light at a second focus (FL2) farther from optic 14, illustrating how mechanical features in an IOL may result in plate effect that could result in off-axis light being perceived as glare. In FIG. 4B, collineated light leaves the light source and passes through optic 14. Optic 14 focuses the light at the first rate of convergence toward the point at the first focal length ($FL_1$). However, FIG. 4B depicts plate $P_2$ having a larger thickness than plate $P_1$ depicted in FIG. 4A. Accordingly, instead of the light being focused at first focal length $FL_1$, plate $P_2$ focuses the light at a second rate of convergence until the light reaches a point at a second focal length ($FL_2$). In the human eye, if the point at $FL_1$ corresponds to the retina but the light is focused at a point at $FL_2$, the image will not be presented properly.

Referring to FIGS. 2 and 3, light 42 that is transmitted parallel with an optical axis (such as optical axis OA depicted in FIG. 1) or at any angle less than the threshold incident angle ($\phi$) relative to the optical axis may be expected to pass through optic 14 only. Light 42 may behave similar to light passing through optic 14 and plate $P_1$ in the diagram depicted in FIG. 4A.

However, light 44 that is transmitted off-axis (i.e., at an angle at or above the threshold incident angle ($\phi$)) may pass through optic 14 and also pass through flange 34, such that off-axis light 44 may behave similar to light passing through optic 14 and plate $P_2$ in the diagram depicted in FIG. 4B. For example, if this off-axis light 44 passes through optic 14 and flange 34 having a flange posterior surface 40a parallel to flange anterior surface 38 (as depicted in FIG. 2), a plate effect may occur and result in visible glare artifacts or other undesirable effects. To reduce the likelihood of glare, double-image dysphotopsia, and other unwanted effects, embodiments of IOL 10 comprise flange 34 formed with a profile of flange posterior surface 40b non-parallel to flange anterior surface 38 (as depicted in FIG. 3) such that off-axis light 44 passing through optic 14 and flange 34 is defocused. Defocusing light may include redistributing off-axis light 44 such that, for light entering IOL 10 at an incident angle greater than a threshold angle and transmitted through both optic 14 and flange 34, no focal length exists.

Plate Effect Based on Flange Design

Figure 5A:
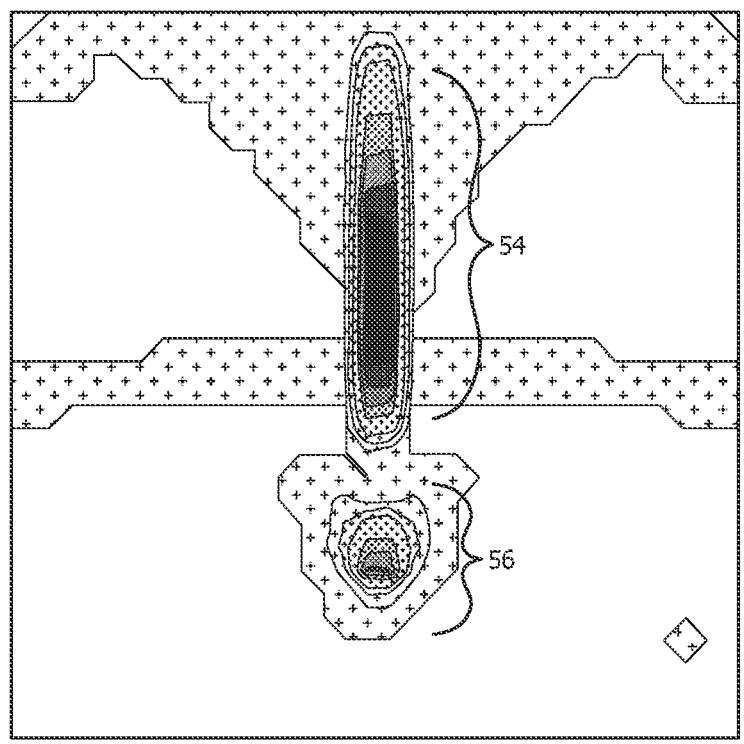
FIG. 5A depicts a simulated irradiance image, illustrating a distribution of light and a glare artifact caused by off-axis light transmitted through the optic and the flange described in FIG. 2.
Figure 5B:
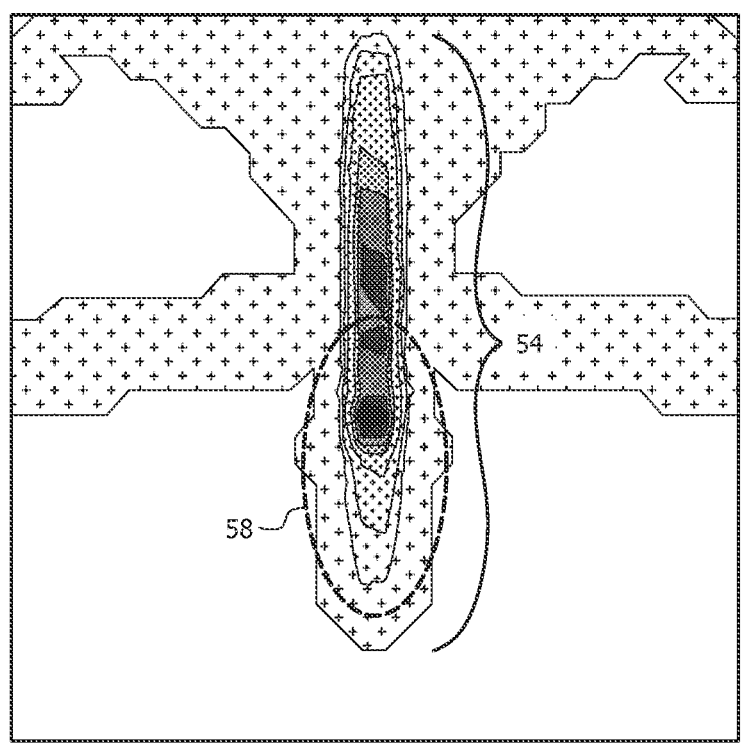
FIG. 5B depicts a simulated irradiance image, illustrating a distribution of light including off-axis light transmitted through the optic and the flange described in FIG. 3.

To illustrate the effect that flange design has on off-axis light distribution, FIGS. 5A and 5B depict simulated light distributions for IOL 10 formed with flange anterior surface 38 and flange posterior surface 40 formed parallel and non-parallel to each other, respectively. FIG. 5A depicts a simulated light distribution associated with flange 34 formed with flange posterior surface 40a parallel to flange anterior surface 38 (such as depicted in FIG. 2), illustrating a glare artifact. In FIG. 5A, a first portion 54 of the light distribution is associated with light 42 passing through optic 14 at an angle less than the threshold incident angle ($\phi$) and a second portion 56 of the light distribution is associated with off-axis light 44 passing through optic 14 and flange 34. Second portion 56 may result in a glare artifact visible by the patient and is generally undesirable.

FIG. 5B, depicts a simulated light distribution associated with flange 34 formed with flange posterior surface 40b non-parallel to flange anterior surface 38 (such as depicted in FIG. 3), illustrating how flange 34 formed with flange posterior surface 40b non-parallel to flange anterior surface 38 may reduce or even or mitigate plate effect in IOL 10. In FIG. 5B, first portion 54 of the light distribution is associated with light 42 passing through optic 14 at an angle less than the threshold incident angle ($\phi$) and a second portion 58 of the light distribution is associated with off-axis light 44 passing through optic 14 and flange 34. The effect of defocusing the second portion 58 of light 44 to overlap the first portion 54 may reduce the glare caused by the plate effect of flange 34 or prevent a glare artifact from being visible by the patient.

A method of manufacturing IOL 10 may include selecting optic 14 for implanting in a patient, including identifying a radius of curvature for optic anterior surface 14a, a radius of curvature for optic posterior surface 14b and an optic thickness 14c. Once optic 14 is selected, ring 16 may be selected or formed to ensure off-axis light transmitted through optic 14 and flange 34 does not create a glare effect. In some embodiments, ring 16 depicted in FIG. 2 may be selected as a starting design, and a ray-tracing program or other computer simulation may facilitate determining the likelihood that ring 16 will produce a glare effect. If a glare effect is possible, IOL 10 may be modified to ensure flange posterior surface 40b is non-parallel with flange anterior surface 38 such as depicted in FIG. 3.

Flange anterior surface 38 and flange posterior surface 40b may each be straight or curved, may be concave or convex, and have other profiles as long as a profile of flange posterior surface 40b is non-parallel with a profile of flange anterior surface 38. For example, flange anterior surface 38 and flange posterior surface 40b may both be concave as long as flange posterior surface 40b is non-parallel with flange anterior surface 38. Furthermore, the outer diameter of flange 34 (i.e., where flange anterior surface 38 transitions to posterior rim anterior surface 30) may depend on one or more factors or features of IOL 10. For example, the outer diameter of flange 34 may depend on optic 14, the threshold incident angle ($\phi$) at which off-axis light is likely to cause glare, and the profile of flange posterior surface 40b or flange anterior surface 38. The profile of flange posterior surface 40b may be modified to focus light at a focal length in front of or behind the focal length associated with optic 14 or may generally defocus light.

Once optic 14 and ring 16 with flange 34 having flange posterior surface 40b non-parallel with flange anterior surface 38 are selected, optic 14 and ring 16 may be assembled to form IOL 10.

A modular IOL 10, including base 12 and optic 14, may be implanted using various surgical techniques. A modular IOL 10 may be implanted by initially delivering base 12 into the capsular bag in a rolled configuration using an injector (a.k.a., inserter or delivery tube) inserted through a corneal incision, through the capsulorhexis, and into the capsular bag.

Base 12 may be ejected from the injector and allowed to unfurl. With gentle manipulation, haptics 18 of base 12 engage the inside equator of the lens capsule and center the ring 16 relative to the capsulorhexis. Haptics 18 may facilitate handling of base 12 and indicate an orientation of base 12.

Optic 14 may also be delivered in a rolled configuration using an injector, positioning the distal tip thereof adjacent base 12. Optic 14 may be ejected from the injector and allowed to unfurl. With gentle manipulation, optic 14 is centered relative to the capsulorhexis. Optic 14 may have features (not shown) for ease of insertion into a capsular bag, for removal of optic 14 from a capsular bag, and to help align optic 14 relative to base 12.

Once optic 14 has been delivered and unfurled in the capsular bag, optic 14 may be positioned in ring 16 in base 12.

If needed, IOL 10 including optic 14 and base 12, may be removed by generally reversing the steps described above.

A probe or similar device may enter the capsular bag containing modular IOL 10. A probe or similar device may engage optic 14. With gentle manipulation, optic 14 may be lifted such that optic 14 and base 12 are disconnected. The probe may remove one or more of optic 14 and base 12.

A modular intraocular lens (IOL) with a flange for defocusing light associated with off-axis light transmitted through the optic and the flange have been described. The systems have been described in accordance with the exemplary embodiments shown, and one of ordinary skill in the art will readily recognize that there could be variations to the embodiments, and any variations would be within the spirit and scope of the method and system. Accordingly, many modifications may be made by one of ordinary skill in the art without departing from the spirit and scope of the appended claims.

We claim:

1. A modular intraocular lens (IOL), comprising:
    an optic comprising an anterior surface and a posterior surface; and
    an annular ring comprising:
        an anterior rim with an anterior opening; and
        a posterior rim with a flange, wherein:
            the anterior rim and the posterior rim form an inwardly facing recess;
            a flange anterior surface defines a first profile; and
            a flange posterior surface defines a second profile, wherein the second profile is non-parallel with the first profile, and wherein the flange posterior surface comprises a convex curvature having a posteriorly-extending protrusion.

2. The modular IOL of claim 1, wherein:
    the first profile is associated with a first radius of curvature; and the second profile is associated with a second radius of curvature.

3. The modular IOL of claim 1, wherein:
    the flange defines a posterior rim opening with an inner diameter less than a diameter of the anterior rim opening.

4. The modular IOL of claim 3, wherein:
    the optic is shaped to focus light transmitted parallel to an optical axis at a first focal length; and
    the flange is configured to defocus light transmitted through the optic at an incident angle off-axis from the optical axis.

5. The modular IOL of claim 4, wherein:
    the incident angle is greater than 25 degrees off-axis.

6. The modular IOL of claim 1, wherein:
    the flange anterior surface is shaped to support the optic.

7. An intraocular lens assembly, comprising:
    an optic defined by an optic anterior surface having a first curvature and an optic posterior surface having a second curvature;
    a ring for positioning the optic in an intracapsular bag, the ring comprising:
        an anterior rim defining an anterior rim opening with an inner diameter sized to allow insertion of the optic into the ring;
        an inwardly facing recess for retaining the optic in the ring;
        a posterior rim defining a posterior rim opening; and
        a flange formed on the posterior rim, comprising a flange inner diameter less than a diameter of the optic, wherein:
            a flange anterior surface defines a first profile; and
            a flange posterior surface defines a second profile, wherein the second profile is non-parallel with the first profile, and wherein the flange posterior surface comprises a convex curvature having a posteriorly-extending protrusion.

8. The IOL assembly of claim 7, wherein:
    the first profile is associated with a first radius of curvature; and the second profile is associated with a second radius of curvature.

9. The IOL assembly of claim 7, wherein:
    an outer diameter of the flange is greater than an inner diameter of the anterior rim and less than a diameter of the inwardly facing recess.

10. A method of manufacturing a ring for an intraocular lens (IOL), the method comprising:
    forming an anterior rim with an anterior rim opening, the anterior rim opening having a diameter less than a diameter of an optic;
    forming a posterior rim defining a posterior rim opening; and
    forming a flange relative to the posterior rim, comprising:
        forming a flange anterior surface with a first profile; and
        forming a flange posterior surface with a second profile non-parallel with the first profile, wherein the flange posterior surface comprises a convex curvature having a posteriorly-extending protrusion.

11. The method of claim 10, wherein:
    one or more of the cross-section profile of the flange anterior surface, the cross-section profile of the flange posterior surface and the axial distance between the flange anterior surface and the flange posterior surface are formed to defocus off-axis energy passing through the ring.

12. The method of claim 10, further comprising:
    forming an inwardly facing recess on an interior surface of the ring for retaining an optic in the ring.

* * * * *